United States Patent [19]

Hashimoto et al.

[11] 3,935,266

[45] Jan. 27, 1976

[54] N-SUBSTITUTED GUANIDINO ACID DERIVATIVES

[75] Inventors: Sadao Hashimoto; Ryuji Sakakibara; Yasushi Kurashige; Katsuo Takikawa; Yoko Osame; Hiroshi Minami; Takashi Suzue, all of Naruto, Japan

[73] Assignee: Taiho Pharmaceutical Company, Limited, Tokyo, Japan

[22] Filed: Oct. 26, 1971

[21] Appl. No.: 192,557

[30] Foreign Application Priority Data

Oct. 28, 1970 Japan .............................. 45-95341

[52] U.S. Cl. ...... 260/561 A; 260/404.5; 260/471 A; 260/518 A; 260/519; 260/534 R; 260/558 A; 260/559 A; 260/559 S; 260/557 R; 260/561 K; 260/562 N; 424/320

[51] Int. Cl.$^2$ .................................... C07C 103/30

[58] Field of Search ........ 260/561 A, 561 K, 558 A, 260/557 R, 562 N

[56] References Cited

UNITED STATES PATENTS

| | | | |
|---|---|---|---|
| 3,499,927 | 3/1970 | Badcock et al. | 260/564 |
| 3,737,443 | 6/1973 | Hashimoto et al. | 260/404.5 |

FOREIGN PATENTS OR APPLICATIONS

| | | | |
|---|---|---|---|
| 5,924 M | 4/1968 | France | 260/561 A |

OTHER PUBLICATIONS

CA. -1962, Vol. 57, 14129f, Thoai, N.V.

*Primary Examiner*—Ethel G. Love
*Attorney, Agent, or Firm*—Larson, Taylor & Hinds

[57] ABSTRACT

An N-substituted guanidino acid derivatives having the following formula of $$\begin{matrix} ANH \\ NH \end{matrix} \!\!>\! CNH(CH_2)_nCONHR$$

wherein R is an alkyl having 6 to 15 carbon atoms,. a cycloalkyl having 6 to 15 carbon atoms or an aryl($C_6$ to $C_8$)alkyl($C_1$ to $C_9$); A represents $R^1$ or $R_2CO$—, $R^1$ being an alkyl having 1 to 4 carbon atoms, an alkenyl having 2 to 4 carbon atoms, cyclohexyl, a phenyl containing or not containing a substitute of a lower alkyl, a halogenated lower alkyl, a lower alkoxy, hydroxy or a halogen, or a benzyl containing or not containing a substitute of a lower alkyl, a halogenated lower alkyl, a lower alkoxy, hydroxy or a halogen, and $R^2$ being an alkyl of 1 to 3 carbon atoms, an alkenyl of 2 to 3 carbon atoms, an aryl of 6 to 8 carbon atoms or an aryl($C_6$ to $C_8$)alkyl($C_1$ to $C_2$); and n is an integer of 4 to 10. The present compounds are excellent in pharmacological activities, particularly in antagonism to bradykinin and histamine, and useful as anti-inflammatory agent.

3 Claims, No Drawings

N-SUBSTITUTED GUANIDINO ACID DERIVATIVES

This invention relates to N-substituted guanidino acid derivatives and salts thereof having a high order of pharmacological acitivity and to a process for manufacturing the same.

The N-substituted guanidino acid derivatives of the invention are of the following formula:

$$\begin{matrix} ANH \\ NH \end{matrix} \!\!> CNH(CH_2)_nCONHR \qquad (1)$$

wherein R is an alkyl having 6 to 15 carbon atoms, a cycloalkyl having 6 to 15 carbon atoms or an aryl($C_6$ to $C_8$)alkyl($C_1$ to $C_9$); A represents $R^1$ or $R^2CO$—, $R^1$ being an alkyl having 1 to 4 carbon atoms, an alkenyl having 2 to 4 carbon atoms, a cyclohexyl, a phenyl containing or not containing a substitute of a lower alkyl, a halogenated lower alkyl, a lower alkoxy, hydroxy or a halogen, or a benzyl containing or not containing a substitute of a lower alkyl, a halogenated lower alkyl, lower alkoxy, hydroxy or a halogen, and $R^2$ being an alkyl of 1 to 3 carbon atoms, an alkenyl of 2 to 3 carbon atoms, an aryl of 6 to 8 catbon atoms or an aryl($C_6$ to $C_8$)alkyl($C_1$ to $C_2$); and n is an integer of 4 to 10.

The present amide derivatives having the above formula I and salts thereof are solid or oily substances and are excellent in pharmacological activity, particularly in antagonism to bradykinin and to histamine. For example, the present compounds exhibit a high order of depressive action on bradykinin and histamine at a low concentration of $10^{-5}$ to $10^{-6}$ mol/liter when tested using isolated uterus of a rat. Further, the present compounds display excellent depressive acion on accelleration of vascular permeability. Moreover, they have excellent depressive action on edema of heel of a rat due to bradykinin, carrageenin or dextran. Thus the present compounds are useful particularly as anti-inflammatory agents.

The preferred examples of the amide compounds of the invention are listed in Table 1 below:

Table 1

$$\begin{matrix} ANH \\ NH \end{matrix} \!\!> CNH(CH_2)_nCONHR$$

| Comp. No. | A | —$(CH_2)_n$— | R | Properties |
|---|---|---|---|---|
| 1 | $CH_3$— | —$(CH_2)_5$— | —$(CH_2)_5CH_3$ | m.p. 63 – 65°C |
| 2 | $CH_3$— | —$(CH_2)_5$— | —$(CH_2)_9CH_3$ | m.p. 93 – 95°C |
| 3 | $CH_3$— | —$(CH_2)_5$— | —$(CH_2)_{11}CH_3$ | m.p. 95 – 96°C |
| 4 | $CH_3$— | —$(CH_2)_5$— | —$(CH_2)_{13}CH_3$ | m.p. 120°C |
| 5 | $CH_3$— | —$(CH_2)_5$— | —$CH_2CH_2$—[phenyl] | Viscous oil |
| 6 | $CH_3(CH_2)_3$ | —$(CH_2)_5$— | —$(CH_2)_9CH_3$ | m.p. 149 – 152°C |
| 7 | $CH_2$=$CH.CH_2$— | —$(CH_2)_5$— | —$(CH_2)_9CH_3$ | m.p. 115 – 117°C |
| 8 | [cyclohexyl]— | —$(CH_2)_5$— | —$(CH_2)_9CH_3$ | Viscous oil |
| 9 | [phenyl]— | —$(CH_2)_5$— | —$(CH_2)_9CH_3$ | m.p. 106 – 108°C |
| 10 | HO—[phenyl]— | —$(CH_2)_5$— | —$(CH_2)_9CH_3$ | m.p. 73 – 75°C |
| 11 | $F_3C$—[phenyl]— | —$(CH_2)_5$— | —$(CH_2)_9CH_3$ | m.p. 110 – 112°C |
| 12 | $OCH_3$—[phenyl]— | —$(CH_2)_5$— | —$(CH_2)_9CH_3$ | m.p. 113 – 114°C |
| 13 | [phenyl]—$CH_2$— | —$(CH_2)_5$— | —$(CH_2)_9CH_3$ | m.p. 134 – 135°C |
| 14 | $CH_3CO$— | —$(CH_2)_5$— | —$(CH_2)_9CH_3$ | m.p. 88 – 89°C |
| 15 | $CH_3(CH_2)_2CO$— | —$(CH_2)_5$— | —$(CH_2)_9CH_3$ | Viscous oil |
| 16 | $OCH_3$—[phenyl]—CO— | —$(CH_2)_5$— | —$(CH_2)_9CH_3$ | Viscous oil |

Note:
1. Melting points of the compounds Nos. 1 and 4 show those of p-toluene sulfonate monohydrate thereof.
2. Melting points of the compounds Nos. 2 and 3 show those of p-toluene sulfonate hemihydrate thereof.
3. Melting point of the compound No. 6 shows that of monohydrate thereof.
4. Melting point of the compound No. 9 shows that of hemihydrate thereof.
5. Melting point of the compound No. 10 shows that of hydrochloride monohydrate thereof.
6. Melting point of the compound No. 12 shows that of picrate thereof.
7. Melting point of the compound No. 14 shows that of hydrochloride thereof.

Of these compounds particularly preferable are ε-(N-methylguanidino)caproyl-n-decyl amide and ε-(N-acetylguanidino)caproyl-n-decyl amide, since those compounds exhibit higher order of pharmacological activities.

To clarify the pharmacological activities of the present compounds the following tests were performed.

1. Antagonistic action on bradykinin a. Depressive action on contraction of smooth muscle Using ε-(N-methylguanidino)caproyl-n-decyl amide and ε-(N-acetylguanidino)caproyl-n-decyl amide, the depressive effect thereof to the contraction by bradykinin on isolated uterus muscle of rats was tested. The both compounds exhibited 50% depressive action at a concentration of $7.5 \times 10^{-6}$ mol/liter and $1.5 \times 10^{-5}$ mol/liter respectively.

b. Depression of vascular permeability

Using ε-(N-methylguanidino)caproyl-n-decyl amide and ε-(N-acetylguanidino)caproyl-n-decyl amide, the depressive action thereof on acceleration of vascular permeability found in intracutaneous administration of bradykinin to rabits, rats and mice was tested. The compounds tested were orally administered to the animals. A marked depressive action was exhibited with a dose of 100 mg/kg.

2. Depressive action on edema

The compounds of the invention shown in Table 2 below were orally administered to six male rats in each group, weighing 150 ± 10 g and kept to abstain from food for 16 hours. The amount administered was 100 mg per kg of rat. One hour after the administration 1 weight percent aqueous solution of carrageenin was intracutaneously administered in an amount of 0.1 ml per rat to the heel of rat. The volume of edema on heel was measured in 1 hour, 2 hours, 3 hours and 4 hours after the administration of carrageenin and depression rate on edema was determined by the following equation.

$$(A - B)/A$$

A: Volume of edema on the heel of rat administered with carrageenin without administration of the present compound.

B: Volume of edema on the heel of rat administered with the present compound and carrageenin.

The results are shown in Table 2 below, in which compound number represents the compound with the corresponding number given in Table 1.

Table 2

| Comp. No. | Depressive action on edema (%) Times (hr) after administration 1 | 2 | 3 | 4 |
|---|---|---|---|---|
| 1 | 58.7 | 36.2 | 23.1 | 10.7 |
| 2 | 54.9 | 61.7 | 53.0 | 43.2 |
| 3 | 50.6 | 42.7 | 37.9 | 26.8 |
| 4 | 32.2 | 35.4 | 50.9 | 36.9 |
| 5 | 40.6 | 32.2 | 25.4 | 23.6 |
| 6 | 42.5 | 40.8 | 39.4 | 31.2 |
| 7 | 34.7 | 28.6 | 20.0 | 18.7 |
| 8 | 31.2 | 24.3 | 16.4 | 15.2 |
| 9 | 48.8 | 27.8 | 24.9 | 17.6 |
| 10 | 32.5 | 30.1 | 24.3 | 20.1 |
| 11 | 44.6 | 39.5 | 37.4 | 34.3 |
| 12 | 33.8 | 24.6 | 20.1 | 18.8 |
| 13 | 30.7 | 21.6 | 15.2 | 14.8 |
| 14 | 39.7 | 41.4 | 51.0 | 52.5 |
| 15 | 24.2 | 18.8 | 15.8 | 14.8 |
| 16 | 22.0 | 13.5 | 29.0 | 25.1 |

The amide derivatives of the invention may be prepared by various methods. According to one of the preferred methods an N-substituted guanidino acid having the formula (II) below is reacted with a lower alkylchloroformate of the formula (II) below to produce a mixed anhydride of the formula (IV) below and the resultant mixed anhydride (IV) is then reacted with an amine derivative of the formula (V) to produce the desired N-substituted ω-guanidino acid amide (I). This method is hereinafter referred to as "Method-A" and the reaction involved therein are shown by the following equations:

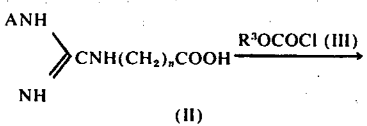

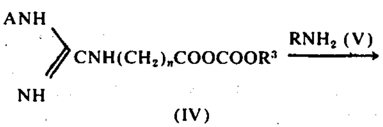

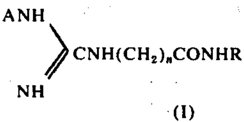

wherein A, R and n are the same as defined before and $R^3$ is a lower alkyl.

The starting N-substituted guanidino acid (II) used in this Method-A can be prepared by reacting isothiourea derivatives, isourea derivatives or salts thereof having the formula (VI) below with ω-aminoacid having the formula (VII) below:

The reaction equation is shown below:

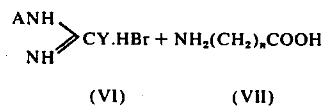

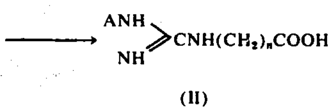

wherein R, A and n are the same as defined before, Y is a lower alkoxyl or lower alkylmercapto group.

This reaction can be conducted in the presence of a solvent. The solvent used includes water and methanol, ethanol or the like lower alcohol. It is preferable to adjust the reaction system to alkalinity of a pH of 9 to 12 by adding alkali such as sodium hydroxide, potassium hydroxide, sodium bicarbonate, sodium carbonate, etc. Of these sodium bicarbonate or sodium carbonate may be used when lower alcohol is employed as a reaction medium. The reaction can preferably be conducted under reflux conditions.

Examples of the starting guanidino acid (II) used in Method-A are ε-(N-methylguanidino)caproic acid, ε-(N-p-hydroxyphenylguanidino)caproic acid, ε-(N-m-trifluoromethylphenylguanidino)caproic acid, ε-(N-benzylguanidino)caproic acid, etc.

In carrying out the reaction of the N-substitute guanidino acid (II) with alkylchloroformate (III) it is preferred to add dropwise the lower alkylchloroformate (III) to a solution of the N-substituted guanidino acid (II) dissolved in a solvent. When the N-substituted guanidino acid (II) is hardly soluble in a solvent it is preferably used in the form of acid salt. The lower alkylchloroformate (III) is preferably used in an equivalent amount. The examples of the solvents used are N,N-dimethylformamide, acetonitrile, chloroform, etc. The reaction temperature is usually in the range of −10° to 10°C. If desired, hydrogen halide acceptor may be added to the reaction system to accelerate the reaction. Examples of the hydrogen halide acceptors are triethylamine, tributyl amine, etc. The acceptor is usually used in an equivalent amount to the starting N-substituted guanidino acid used. In general the reaction completes within about 15 minutes, whereby the intermediate, mixed anhydride (IV) is obtained. The resultant mixed anhydride (IV) can be subjected to the subsequent reaction with an amine derivative (V) as it is in the reaction mixture resulting from the preceding step. According to the preferred method the amine derivative (V), is added dropwise with stirring at a temperature of −10° to 10°C to the resultant reaction mixture. The amine derivatives can be used as it is or in the form of a solution dissolved in organic solvents, such as dimethylformamide, acetonitrile, chloroform, etc. After the addition of the amine derivatives (V) it is preferable to stir the reaction system at −10° to 10°C and thereafter to continue the stirring at room temperature. The reaction mixture is then left standing at room temperature overnight to complete the reaction.

The desired product (I) thus produced can be isolated from the resultant reaction mixture, for example, by concentrating the reaction mixture and adding an alkali solution to the concentrate to precipitate the product, followed by recrystallization. If the product is not crystalline substance it can be precipitated in the form of acid salt such as p-toluenesulfonate, hydrochloride, etc.

According to another preferred method for preparing the present amide derivatives, ω-aminoacid derivatives having the formula (VIII) is reacted with isothiourea derivatives, isourea derivatives or salts thereof having the formula (VI) before. This method is hereinafter referred to as "Method-B" and the reaction involved therein is shown by the following equation:

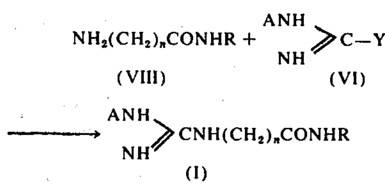

wherein R, A, Y and n are the same as defined before.

The starting ω-aminoacid derivatives (VIII) used in the above Method-B are known in the art and easily prepared by the method shown in the following equations

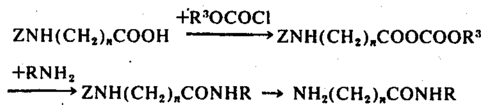

wherein R, $R^3$ and n are the same as defined before and Z is a blocking group of amino radical.

The reaction of Method-B can be conducted in the presence of a solvent, such as methanol, ethanol, chloroform, etc. Preferably the reaction may be carried out under reflux condition. The reaction usually completes within a period of 5 to 10 hours. The product thus obtained is isolated by the same manner as described in Method-A before.

According to another preferred method the present amide derivatives (I) in which A in the formula (I) is $R^2CO$ are prepared by reacting ω-guanidino acid derivatives having the formula (IX) below with acylhalide having the formula (X) or acid anhydride having the formula (XI). This reaction is hereinafter referred to as "Method-C" and the reaction involved therein is shown by the following equation:

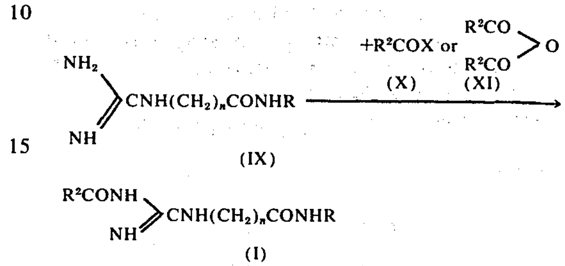

wherein R, $R^2$ and n are the same as defined before and X is a halogen atom.

The preparation of the starting ω-guanidino acid derivatives (IX) is disclosed in detail in our copending application Ser. No. 25,241, filed on Apr. 2, 1970. For example, it is prepared by reducing with hydrogen gas ω-nitroguanidino acid amide derivatives having the formula of

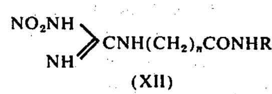

wherein R and *n* are the same as defined before. The ω-nitroguanidino acid amide derivatives are derived from ω-nitroguanidino acid having the formula of

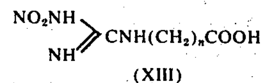

wherein n is the same as defined before. For example, ω-nitroguanidino acid is reacted with a lower alkylchlorocarbonate of the formula of $$R^4OCOCl \qquad (XIV)$$

wherein $R^4$ is a lower alkyl to produce mixed anhydride of the formula of

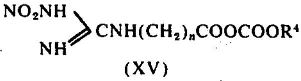

wherein $R^4$ and n are the same as defined before, and the resultant mixed anhydride (XV) is then subjected to the reaction with a primary amine to produce the desired ω-nitroguanidino acid amide derivatives (XII) before.

In the Method-C the acylhalide (X) or acid anhydride (XI) can be used in an equivalent amount or in a slight excess amount. The reaction is conducted in the presence or absence of a solvent. Examples of the solvents are chloroform, benzene, etc. The reaction can be carried out at a room temperature or an elevated temperature, but it is preferable to carry out the reaction under reflux conditions. In general, the reaction completes within a period of 1 to 2 hours. The product obtained can be separated in the same manner as disclosed in Method-A before.

EXAMPLE 1

19.9 g of N-methyl-S-ethyl isothiourea hydrobromide was dissolved in 40 ml of water and to the solution kept at 0° to 5°C was added 5.0 g of sodium hydroxide dissolved in 20 ml of water. To the mixture was added 13.1 g of ε-aminocaproic acid dissolved in 30 ml of hot water and the resultant mixture was left to stand at room temperature overnight. The precipitate thus obtained was filtered, washed with water and dried, whereby 16.8 g of ε-(N-methylguanidino)caproic acid monohydrate having a melting point of 177°– 179°C was obtained with a yield of 81.3%.

Elementary analysis of the product gave the following results:

| | C | H | N |
|---|---|---|---|
| Found: | 46.37% | 9.24% | 20.28% |
| Calcd. for $C_8H_{17}N_3O_2.H_2O$: | 46.19% | 9.50% | 20.38% |

10.4 g of the ε-(N-methylguanidino)caproic acid monohydrate thus obtained was dissolved in dilute hydrochloric acid and concentrated under reduced pressure. The residue was dissolved in 70 ml of N,N-dimethylformamide and to the solution kept at 0° to 5°C was added dropwise 4.75 ml of ethylchloroformate and then 6.75 ml of triethyl amine. After the resultant mixture was stirred for 15 minutes 7.9 g of n-decylamine was added dropwise thereto at 0° to 5°C. The reaction system was stirred at that temperature for 1 hour and then at room temperature for 1 hour and left to stand at room temperature overnight. The resultant reaction mixture was concentrated under reduced pressure and cold 1N sodium hydroxide was added to the residue to separate oily substance. Ether was added thereto and the mixture was cooled, whereby crystalline substance was precipitated. The precipitated substance was separated by filtration and dissolved in chloroform. 8.6 g of toluene sulfonic acid added to the solution. The mixture was concentrated under reduced pressure and the recrystallization from ethanol-ether extract of the condensed mixture gave 17.3 g of a crystalline solid of ε-(N-methylguanidino) caproyl-n-decyl amide p-toluenesulfonate hemihydrate having a melting point of 93° to 95°C. The yield was 68.3%.

Elementary analysis of the product gave the following results:

| | C | H | N |
|---|---|---|---|
| Found: | 59.14% | 9.33% | 11.03% |
| Calcd. for $C_{18}H_{38}N_4O.C_7H_8O_3S.½H_2O$: | 59.03% | 9.41% | 11.23% |

EXAMPLE 2

10.4 g of ε-(N-methylguanidino)caproic acid monohydrate obtained in the same manner as in Example 1 was added to dilute hydrochloric acid and concentrated under reduced pressure. The residue was dissolved in 70 ml of N,N-dimethylformamide. To the solution kept at 0° to 5°C was added dropwise 4.75 ml of ethylchloroformate and then 6.75 ml of triethylamine. After being stirred at that temperature, 11.3 g of n-tetradecylamine was added dropwise at 0° to 5°C and further stirred at that temperature for 1 hour and then at room temperature for 1 hour. The resultant mixture was left to stand at room temperature overnight. The reaction mixture thus obtained was concentrated under reduced pressure and cold 1N sodium hydroxide was added to the residue for precipitation. The precipitated oily substance was separated and ether was added thereto. The resultant mixture was left to stand under cooling to precipitate crystalline solid. The crystalline solid was separated by filtration and recrystallized from ethanol-ether to give 13.1 g of ε-(N-methylguanidino)-caproyl-n-tetradecylamide monohydrate having a melting point of 120°C. The yield was 65.2%.

Elementary analysis of the product gave the following results:

| | C | H | N |
|---|---|---|---|
| Found: | 65.96% | 12.08% | 13.99% |
| Calcd. for $C_{22}H_{46}N_4O.H_2O$: | 65.61% | 12.13% | 13.80% |

EXAMPLE 3

To 50 ml of ethanol were added 8.3 g of hydrobromic acid salt of N-(p-hydroxyphenyl)-S-ethyl isothiourea, 4.0 g of ε-aminocaproic acid and 5.0 g of sodium bicarbonate and the mixture was refluxed with stirring for 10 hours. After being cooled, the resultant reaction mixture was filtered and the product was washed with water. Recrystallization from acetic acid-ether gave 5.8 g of ε-(N-p-hydroxyphenylguanidino) caproic acid hemihydrate having a melting point of above 200°C. Yield was 70.7%.

Elementary analysis of the product gave the following results:

| | C | H | N |
|---|---|---|---|
| Found: | 56.92% | 7.35% | 15.32% |
| Calcd. for $C_{13}H_{19}N_3O_3.½H_2O$: | 57.03% | 7.31% | 15.32% |

2.7 g of ε-(N-p-hydroxyphenylguanidino)caproic acid hemihydrate was dissolved in dilute hydrochloric acid and concentrated under reduced pressure. The residue was dissolved in 30 ml of N,N-dimethylformamide and to the solution kept at 0° to 5°C was added dropwise 0.96 ml of ethylchloroformate and then 1.39 ml of triethylamine. After the mixture was stirred for 15 minutes, 1.6 g of n-decylamine was added dropwise to the mixture at 0° to 5°C. Thereafter, the reaction was carried out in the same manner as in Example 1. The resultant reaction mixture was concentrated under reduced pressure and cold 1N sodium hydroxide was added to the residue to separate precipitated oily substance. The precipitated oily substance was washed with ether and extracted with chloroform after being turned acidic by addition of hydrochloric acid. The chloroform layer was washed with water and dried with sodium sulfate, followed by concentration. Recrystallization of the residue from chloroformether gave 2.8 g of ε-(N-p-hydroxyphenylguanidino) caproyl-n-decyl amide hydrochloride monohydrate having a melting point of 73° to 75°C. The yield was 60.8%.

Elementary analysis of the product gave the following results:

| | C | H | N |
|---|---|---|---|
| Found: | 60.18% | 9.44% | 12.20% |
| Calcd. for $C_{23}H_{30}N_4O_2.HCl.H_2O$: | 60.43% | 9.34% | 12.40% |

EXAMPLE 4

To 100 ml of ethanol were added 18.1 g of N-(m-trifluoromethylphenyl)-S-ethylisothiourea hydrobromate, 7.9 g of ε-aminocaproic acid and 9.2 g of sodium bicarbonate and the mixture was refluxed with stirring for 10 hours. After being cooled, the resultant reaction mixture was filtered, washed with water and dried. Recrystallization from acetic acid-ether gave 15.2 g of ε-(N-m-trifluoromethylphenylguanidino)caproic acid acetate having a melting point of 155° to 156°C. The yield was 73.1%.

Elementary analysis of the product gave the following results:

| | C | H | N |
|---|---|---|---|
| Found: | 50.93% | 5.88% | 11.14% |
| Calcd. for $C_{14}H_{18}F_3N_3O.CH_3COOH$: | 50.73% | 5.61% | 11.29% |

3.8 g of ε-(N-m-trifluoromethylphenylguanidino)caproic acid acetate thus obtained was dissolved in dilute hydrochloric acid and concentrated under reduced pressure. The residue was dissolved in 30 ml of N,N-dimethylformamide. To the solution kept at 0° to 5°C was added dropwise 0.96 ml of ethylchloroformate and then 1.39 ml of triethylamine. The mixture was stirred at that temperature for 15 minutes and 1.6 g of n-decylamine was added dropwise thereto at the same temperature. Thereafter the reaction was carried out in the same manner as in Example 1. After the reaction the resultant reaction mixture was concentrated under reduced pressure and cold 1N sodium hydroxide was added to the residue. The mixture was cooled to precipitate crystalline solid. The crystalline solid was separated by filtration and recrystallized from chloroform-petroleum ether, whereby 2.9 g of ε-(N-m-trifluoromethylphenylguanidino)caproyl-n-decyl amide having a melting point of 110° to 112°C. The yield was 63.0%.

Elementary analysis of the product gave the following results:

| | C | H | N |
|---|---|---|---|
| Found: | 63.13% | 8.61% | 12.27% |
| Calcd. for $C_{24}H_{39}N_4OF_3$: | 62.85% | 8.42% | 12.37% |

EXAMPLE 5

In 150 ml of ethanol were added 27.5 g of N-benzyl-S-ethylisothiourea hydrobromide, 13.1 g of ε-aminocaproic acid and 16.8 g of sodium bicarbonate and the mixture was refluxed with stirring for 12 hours. After being cooled, the mixture was filtered and washed with water. The product thus obtained was recrystallized from acetic acid-ether, whereby 25.3 g of ε-(N-benzylguanidino)caproic acid acetate having a melting point of 134 to 135°C was obtained. The yield was 78.3%.

Elementary analysis of the product gave the following results:

| | C | H | N |
|---|---|---|---|
| Found: | 59.42% | 7.79% | 12.99% |
| Calcd. for $C_{14}H_{21}N_3O_2.CH_3COOH$: | 59.15% | 7.81% | 12.88% |

10.7 g of the ε-(N-benzylguanidino)caproic acid acetate was dissolved in dilute hydrochloric acid and the solution was concentrated under reduced pressure. The residue was dissolved in 60 ml of N,N-dimethylformamide. To the solution kept at 0° to 5°C was added dropwise 3.2 ml of ethylchloroformate and then 4.6 ml of triethylamine. After the resultant mixture was stirred for 15 minutes 5.2 g of n-decylamine was added dropwise thereto at 0° to 5°C. Thereafter the reaction was carried out in the same manner as in Example 1. After the reaction, the resultant reaction mixture was concentrated under reduced pressure and cold 1N sodium hydroxide was added to the residue. The resultant alkaline mixture was cooled to precipitate crystalline solid. The precipitated solid was recovered by filtration and recrystallized from chloroform-ether to give 8.2 g of ε-(N-benzylguanidino)-caproyl-n-decylamide having a melting point of 131° to 133°C. The yield was 61.7%.

Elementary analysis of the product gave the following results:

| | C | H | N |
|---|---|---|---|
| Found: | 71.60% | 10.51% | 13.92% |
| Calcd. for $C_{24}H_{42}N_4O$: | 71.53% | 10.90% | 13.65% |

EXAMPLE 6

In 50 ml of chloroform were dissolved 10.6 g of carbobenzoxyaminocaproic acid and 5.4 ml of triethylamine and to the solution kept at 0° to 5°C was added dropwise 3.8 ml of ethylchloroformate. After the mixture was stirred for 15 minutes, 6.3 g of n-decylamine was added thereto at 0° to 5°C. The mixture was stirred at that temperature for 1 hour and at room temperature for 1 hour, and thereafter left to stand overnight. The resultant reaction mixture was washed with 1N hydrochloric acid, with water, then with 1N sodium hydroxide and finally with water and subjected to concentration under reduced pressure. The residue was recrystallized from ethanol-water to give 13.2 g of ε-carbobenzoxyaminocaproyl-n-decylamide having a melting point of 101° to 103°C. The yield was 81.2%.

Elementary analysis of the product gave the following results:

| | C | H | N |
|---|---|---|---|
| Found: | 71.25% | 9.97% | 6.92% |
| Calcd. for $C_{24}H_{40}N_2O_3$: | 71.03% | 10.21% | 6.95% |

6 g of the ε-carbobenzoxyaminocaproyl-n-decylamide thus obtained was added to 40 ml of saturated acetic acid solution of hydrogen bromide and the mixture was stirred at room temperature for 1 hour. After the reaction, the reaction mixture was concentrated under reduced pressure and the residue was dissolved in a small amount of ethanol. To the solution was added cold 1N sodium hydroxide to precipitate crystalline solid. The precipitated solid was recovered by filtration and recrystallized from ethanol-ether to give 3.9 g of ε-aminocaproyl-n-decylamide having a melting point of 101° to 103°C. The yield was 92.9%.

Elementary analysis of the product gave the following results:

| | C | H | N |
|---|---|---|---|
| Found: | 68.03% | 12.61% | 9.92% |
| Calcd. for $C_{16}H_{34}N_2O$. $H_2O$: | 67.70% | 12.67% | 9.91% |

To 50 ml of ethanol were added 9.1 g of the ε-aminocaproyl-n-decylamide thus obtained, 7.5 g of N-allyl-S-ethylisothiourea hydrobromide and 5.6 g of sodium bicarbonate and the mixture was refluxed with stirring for 15 hours. After being cooled, the resultant reaction mixture was filtered and the filtrate was concentrated under reduced pressure. The residue was extracted with chloroform and the extract was concentrated. Recrystallization from chloroform-ether gave 8.1 g of ε-(N-allylguanidino)-caproyl-n-decylamide having a melting point of 115° to 117°C. The yield was 71.2%.

Elementary analysis of the product gave the following results:

| | C | H | N |
|---|---|---|---|
| Found: | 68.14% | 11.44% | 15.90% |
| Calcd. for $C_{20}H_{40}N_4O$: | 67.89% | 11.39% | 15.99% |

EXAMPLE 7

To 60 ml of ethanol were added 4.8 g of ε-aminocaproyl-n-decylamide, 4.3 g of N-n-butyl-S-ethylisothiourea hydrobromide and 2.8 g of sodium bicarbonate and the mixture was refluxed for 10 hours. The similar procedures disclosed in Example 6 were followed and recrystallization from 70% ethanol gave 3.3 g of ε-(N-n-butylguanidino)caproyl-n-decylamide having a melting point of 149° to 152°C. The yield was 50.4%.

Elementary analysis of the product gave the following results:

| | C | H | N |
|---|---|---|---|
| Found: | 65.24% | 12.00% | 14.50% |
| Calcd. for $C_{21}H_{44}N_4O.H_2O$: | 65.50% | 11.92% | 14.41% |

EXAMPLE 8

In 30 ml of ethanol were added 2.8 g of ε-aminocaproyl-n-decylamide, 2.6 g of N-phenyl-S-ethylisothiourea hydrobromide and 1.6 g of sodium bicarbonate and the mixture was refluxed for 8 hours. The similar procedures disclosed in Example 6 were followed and recrystallization from ethanol-ether gave 2.9 g of ε-(N-phenylguanidino)caproyl-n-decylamide hemihydrate having a melting point of 106° to 108°C. The yield was 72.5%.

Elementary analysis of the product gave the following results:

| | C | H | N |
|---|---|---|---|
| Found: | 69.48% | 10.39% | 14.09% |
| Calcd. for $C_{23}H_{40}N_4O.½H_2O$: | 69.58% | 10.44% | 14.04% |

EXAMPLE 9

In 100 ml of ethanol were added 18.0 g of ε-aminocaproyl-n-decylamide, 16.1 g of N-(o-methoxyphenyl)-S-ethylisothiourea hydrobromide and 10.6 g of sodium bicarbonate and the mixture was refluxed with stirring for 8 hours. The similar procedures disclosed in Example 6 were followed.

The purification of the product by chloroform-ether gave 17.3 g of ε-(N-o-methoxyphenylguanidino)caproyl-n-decylamide as oily substance, light yellow in color. The yield was 68.3%.

The oily substance was dissolved in ethanol, and aqueous solution of pycric acid was added to the solution to precipitate crystalline solid. Recrystallization thereof from ethanol-ether gave picric acid salt of ε-(N-o-methoxyphenylguanidino)-caproyl-n-decylamide having a melting point of 113 to 114°C.

Elementary analysis of the product gave the following results:

| | C | H | N |
|---|---|---|---|
| Found: | 53.63% | 7.00% | 15.14% |
| Calcd. for $C_{24}H_{42}N_4O_2.C_6H_3O_7$: | 55.31% | 6.80% | 15.10% |

EXAMPLE 10

7.5 g of ε-guanidinocaproyl-n-decylamide was added to 15 ml of acetic anhydride and the mixture was heated at 80°C for 2 hours. The resultant reaction mixture was concentrated under reduced pressure and the residue was dissolved in 20 ml of ethanol. Dry hydrogen chloride gas was passed into the solution for 5 minutes. After concentration under reduced pressure the concentrate was recrystallized from ethanol-ether to give 7.2 g of ε-(N-acetylguanidino)caproyl-n-decylamide hydrochloride having a melting point of 88° to 90°C. The yield was 76.6%.

Elementary analysis of the product gave the following results:

| | C | H | N |
|---|---|---|---|
| Found: | 58.37% | 10.05% | 14.33% |
| Calcd. for $C_{19}H_{38}N_4O_2.HCl$: | 58.12% | 9.87% | 14.54% |

EXAMPLE 11

7.5 g of ε-(N-methylgaunidino)caproic acid monohydrate was dissolved in dilute hydrochloric acid and the solution was concentrated under reduced pressure. The residue was dissolved in 80 ml of N,N-dimethylformamide. To the solution kept at 0° to 5°C was added dropwise with stirring 3.8 ml of ethylchlorocarbonate and then 5.4 ml of triethylamine. After being stirred for 15 minutes, 5 g of β-phenethylamine was added dropwise with stirring at that temperature. After addition the mixture was stirred at 0° to °C for 1 hour and further at room temperature for 1 hour. The mixture was then left to stand at room temperature overnight. Thereafter the resultant reaction mixture was concentrated under reduced pressure and cold 1N sodium hydroxide was added to the residue to precipitate oily substance. The oily substance separated was purified with chloroformether to produce 7.2 g of ε-(N-methylguanidino)-caproyl-β-phenethyl amide, viscous oily substance. Yield was 67.9%.

Infrared spectroscopic analysis of the resultant product gave the following absorption:

3250 $cm_{-}^{1}$, 2950 $cm_{-}^{1}$, 1620 $cm_{-}^{1}$, 1530 $cm_{-}^{1}$, 1400 $cm_{-}^{1}$ and 750 $cm_{-}^{1}$.

EXAMPLE 12

To 100 ml of ethanol were added 7.2 g of ε-aminocaproyl-n-decylamide, 12 g of N-cyclohexyl-S-ethylisothiourea hydrobromide and 15 g of sodium bicarbonate and the mixture was refluxed with stirring for 10 hours. Thereafter the same procedures disclosed in Example 6 were conducted. The product obtained was purified with chloroform-ether, whereby 6.9 g of ε-(N-cyclohexylguanidino)caproyl-n-decyl amide. Yield was 72.6%.

Infrared spectroscopic analysis of the resultant product gave the following absorption:

3300 $cm^{-1}$, 2950 $cm^{-1}$, 1620 $cm^{-1}$, 1550 $cm^{-1}$ and 1450 $cm^{-1}$.

What we claim is:

1. An N-substituted guanidino acid derivative having the following formula of $$\begin{matrix} ANH \\ NH \end{matrix}\!\!>\!CNH(CH_2)_nCONHR$$

wherein R is an alkyl having 6 to 15 carbon atoms or phenethyl; A represents an alkyl having 1 to 4 carbon atoms, an alkenyl having 2 to 4 carbon atoms and cyclo hexyl; and *n* is an integer of 5.

2. ε-(N-methylguanidino)caproyl-n-decyl amide.

3. ε-(N-acetylguanidino)caproyl-n-decyl amide.

* * * * *